United States Patent [19]

Linder et al.

[11] 4,391,691
[45] Jul. 5, 1983

[54] TEMPERATURE COMPENSATED POLAROGRAPHIC OXYGEN GAS SENSOR AND SENSING SYSTEM, PARTICULARLY FOR AUTOMOTIVE APPLICATION

[75] Inventors: Ernst Linder, Muhlacher; Helmut Maurer, Horrheim; Klaus Muller, Tamm; Franz Rieger, Aalen-Wasseralfingen, all of Fed. Rep. of Germany

[73] Assignee: Robert Bosch GmbH, Stuttgart, Fed. Rep. of Germany

[21] Appl. No.: 242,579

[22] Filed: Mar. 11, 1981

[30] Foreign Application Priority Data

Mar. 20, 1980 [DE] Fed. Rep. of Germany ....... 3010632

[51] Int. Cl.³ .................... G01N 27/56; G01N 27/58
[52] U.S. Cl. .................................. 204/408; 204/412; 204/425; 204/426
[58] Field of Search ............... 204/195 S, 1 S; 338/34

[56] References Cited

U.S. PATENT DOCUMENTS

| | | | |
|---|---|---|---|
| 3,691,023 | 9/1972 | Ruka et al. | 204/1 T |
| 3,948,081 | 4/1976 | Wessel et al. | 204/195 S X |
| 3,989,614 | 11/1976 | Tien | 204/195 S |
| 4,151,503 | 4/1979 | Cermak et al. | 204/195 S X |
| 4,306,957 | 12/1981 | Ishitani et al. | 204/195 S |

FOREIGN PATENT DOCUMENTS 1511 4/1979 European Pat. Off. .

Primary Examiner—G. L. Kaplan
Attorney, Agent, or Firm—Frishauf, Holtz, Goodman & Woodward

[57] ABSTRACT

To render output of a polarographic sensor essentially independent of aging of electrodes and temperature effects of the solid electrolyte body, within the operating ranges of the sensor to measure the oxygen composition of exhaust gases, the solid electrolyte plate of, for example, 50 mm length, 8 mm width and 1 mm thickness has a sensing electrode system including a cathode (2), and an anode (3) applied thereto, connected to a voltage source (7) of controllable output voltage. An oxygen molecule diffusion barrier (6) is applied to the cathode electrode. Additionally, a further electrode pair (5,4) is applied to the solid electrolyte body (1), serially connected in the current limiting circuit including the control voltage source. The voltage across one (2,3) of the electrode pairs is measured and compared with the voltage across the other electrode pair (4,5) voltage source, since the resistance of the zirconium solid electrolyte body drops with increasing temperature at roughly the same rate as the increase in limit current flow with increasing temperature. Both electrode pairs (2,3; 4,5) on the solid electrolyte body (1) are exposed to the gases, the oxygen content of which is to be analyzed.

15 Claims, 1 Drawing Figure

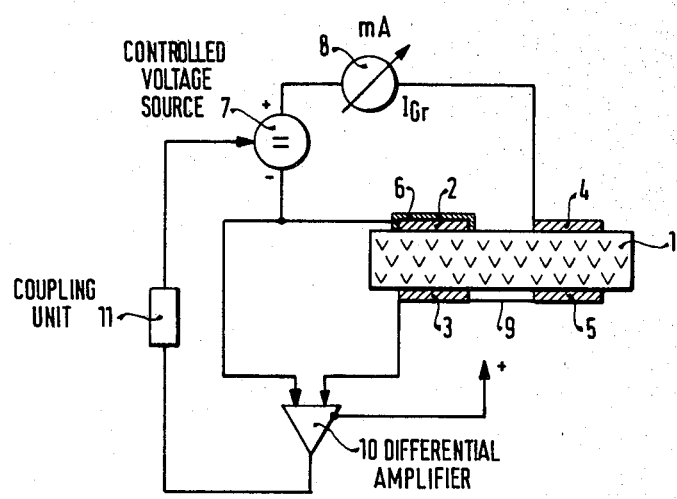

TEMPERATURE COMPENSATED POLAROGRAPHIC OXYGEN GAS SENSOR AND SENSING SYSTEM, PARTICULARLY FOR AUTOMOTIVE APPLICATION

The present invention relates to sensors, and sensing systems to determine the oxygen content in gases, and more particularly the oxygen content in the exhaust gases occurring due to combustion processes in an internal combustion engine.

Various types of sensors and sensing systems have been proposed. One very suitable arrangement particularly for use with internal combustion engines in order to determine the composition of the exhaust gases therefrom, that is, whether the gases are reducing, or oxidizing, is a polarographic sensor in which a solid electrolyte plate has electrodes applied thereon, across which a voltage is applied and the diffusion limiting current is determined. The magnitude of the diffusion limiting current is a measure of the extent of oxygen present in the exhaust gases, assuming a constant applied voltage, and constant, pre-determined operating conditions of the sensor. The diffusion limiting current, upon the presence of excess oxygen, depends on the concentration of oxygen in the gases, if the diffusion of gases to the cathode can control the rate of the resulting reaction.

Polarographic sensors can be so constructed that the anode as well as the cathode electrode are exposed to the gas to be measured. Such sensors are simple in construction and are eminently suitable for mass production manufacture, which is important in automotive applications. Such sensors, however, have the disadvantage that the proportionality of current flow with respect to oxygen concentration in the gases changes due to the changes in temperature of the solid electrolyte. Changes in temperature change the inner resistance of the solid electrolyte. Further, the effects of aging of the electrolytes changes the overall resistance of the sensor element. Thus, a temperature dependent and time-dependent drift of the proportionality of output limiting current with respect to oxygen has been observed. In those applications where accuracy of measurement of the oxygen content in the gases is important, for example in automotive applications where the quality of exhaust gases has to be maintained within accurate pre-determined ranges, it is necessary to recheck, and recalibrate the sensor from time to time.

THE INVENTION

It is an object to provide a sensor, and a sensor system which permits use of sensors under widely varying temperature conditions and in which the effects of aging are self-compensated.

Briefly, a solid electrolyte body, such as stabilized zirconium dioxide has a cathode electrode and an anode electrode applied thereto, both of which are exposed to the exhaust gases.

At least one additional electrode is applied to the sensor chip which is connected in a circuit which senses the internal resistance of the sensor independently of the effects of the contents of gases to which the sensor is exposed. At least one additional electrode, preferably two electrodes are applied to surface portions of the solid electrolyte body to form an oxygen ion conductive ohmic resistance system. This resistance system is serially connected with the actual sensing cathode and anode electrode. To determine the oxygen diffusion limiting current, the sensing cathode electrode is covered with a diffusion barrier which inhibits free access of oxygen, but permits migration of only that quantity of oxygen ion molecules which permit the limiting current to flow. The additional electrodes, which preferably may be similar to the anode and cathode electrodes so that aging phenomena of the cathode and anode electrodes are reflected therein are preferably serially connected with the cathode and anode electrodes. The voltage source for the cathode and anode electrodes has a controllable value, the voltage value of which is controlled as a function of the change of internal resistance as measured in the circuit which includes the further electrode, or electrodes, adjustment of the voltage value of the voltage source permitting compensation for changes of resistance of the solid electrolyte body due to changes in temperature and aging phenomena thereof and/or the electrodes applied thereto.

The sensor, and the sensing system have the advantage that temperature and aging drift is compensated automatically, so that the output indication will be independent of change of the inner resistance of the electrolyte body with respect to temperature and further will be independent of aging of the electrodes. Repeated checking and recalibration of the sensor and the sensor system thus can be eliminated without impairment of accuracy of indication.

In accordance with the preferred feature of the invention, the solid electrolyte body is in the form of a small plate. Preferably, the dimensions of the plate and hence its volume should be as small as possible so that, upon change in temperature, few temperature gradients within the plate will occur. The temperature of a particular region of the plate should be uniform throughout, so that accuracy of indication is insured even though the additional electrode, or electrodes are spaced from the sensing anode/cathode electrode system.

DRAWINGS

The single FIGURE shows, highly schematically, the sensing solid electrolyte plate on which electrodes are applied in accordance with the present invention, in a sensing system which compensates changing temperature and aging, illustrating a simple and reliable electrical network.

The sensor is made of a solid electrolyte plate 1, of stabilized zirconium dioxide. A suitable dimension is, for example, about 50 mm long, 8 mm wide, and 1 mm thick. The plate is held in a suitable socket or housing (not shown) in accordance with any well known construction.

Four electrodes, 2,3,4,5 are applied to the major surfaces of the solid electrolyte plate 1. The electrodes may be made of platinum, or a mixture of platinum and stabilized zirconium dioxide. If a mixture is used, the zirconium dioxide may be about 40% by volume of the electrode mixture. Electrode 2 is connected as a cathode. To operate in the polarographic mode, a diffusion layer or barrier 6 is applied over the cathode electrode 2. The diffusion layer 6 may have the thickness of, about 0.015 mm and is so arranged that gas can reach the cathode electrode 2 only through the diffusion layer. The diffusion layer 6, may, for example, also consist of zirconium dioxide. It is formed with such a porosity that the portion of the overall sensor which includes cathode 2, anode 3, and that portion of the solid electrolyte body 1 between cathode and anode operate within current limiting mode within as wide a range of oxygen partial pressure as possible. Electrodes 2,3,4,5 as well as diffusion barrier 6 can be applied to the solid electrolyte plate 1 by printing-on of material in a suitable paste form.

The sensing unit formed by the solid electrolyte body 1, electrodes 2,3,4,5, and the diffusion barrier 6 is connected into an electrical network to form a sensing system. The electrical network includes a controlled voltage dc source 7. The negative terminal of the voltage source 7, the voltage level of which is controllable, is connected to the cathode 2.

The positive terminal is connected to the electrode 4. A current measuring element, schematically shown as a milliampere meter 8 is connected in the circuit between the negative terminal from voltage source 7, cathode 2, and electrode 4. The current sensor 8 is used to determine the value of the limiting current which can flow. Rather than providing an indicator 8, of course, a suitable sensing element can replace the meter 8 which provides an output signal to control a regulating or control system which, for example, in turn controls the air - fuel composition of an internal combustion engine, and which utilizes the limiting current which flows as a sensing parameter. Control systems of this type are known and do not form part of the present invention.

Electrodes 3 and 5 are connected by a connecting line 9. Electrically, the cathode-anode path of electrodes 2,3 through the portion 1a of the solid electrolyte body 1 and forming the sensing element thereof, and the resistance path between electrode 5,4, including the portion 1b of the solid electrolyte body 1 are serially connected. Cathode and anode electrodes 2,3, with the solid electrolyte body portion 1a form the actual sensor for limiting current sensing portions of the unit; electrodes 5,4 with the portion 1b of the solid electrolyte body 1 interposed form a cell acting as an ohmic resistance. The resistance cell, and the sensing portion are, electrically, serially connected.

In accordance with the present invention, the voltage in cross electrodes 2,3 is controlled to have a value such that under given conditions, the limiting current determined by the instrument or sensor 8 will depend only on the oxygen content of gases to which the sensing unit is exposed, independent of temperature of the unit, or of aging conditions of the electrodes. A differential amplifier 10 is provided, having one input connected across the anode/cathode electrodes, and another input connected to the output of the controlled voltage source. The output of the differential amplifier is connected through a coupling unit 11, which may be a resistor, or a complete coupling network, including amplification to control the voltage level of the controlled voltage source such that the voltage across electrodes 2,3 will have a constant value for uniform conditions in the measuring system, so that the limiting current will accurately reflect changes in the oxygen composition to which the sensing unit is exposed. A suitable value for voltage of the controlled voltage source is between 0.5 and 1.0 V.

All four electrodes, 2,3,4,5 are exposed to the same gaseous atmosphere. They are separated from each other by only a small distance, and are all located within a relatively small space. It can thus be seen that the effects which are due to aging of the electrodes and which would lead to drift of output with respect to time is compensated by the arrangement. Temperature drift, likewise, which is due to the high temperature dependence of the specific resistance of the solid electrolyte body likewise is compensated by the arrangement, as will be shown mathematically. The limiting current $I_{Gr}$ of the cell formed by the electrodes 2,3 and the portion of the solid electrolyte body 1 therebetween increases with increasing temperature from a base value $I_{Gr,O}$, in accordance with an exponential function:

$$I_{Gr} = I_{Gr,O} \cdot e^{a(T-TO)}, \tag{1}$$

wherein $I_{Gr}$ is a limiting current at a temperature T; $I_{Gr,O}$ is a limiting current at a temperature $T_O$; and a is a constant.

The voltage drop due to the internal resistance R of the solid electrolyte body 1 between the electrodes 4 and 5, defined by $U_{ref}$ is:

$$U_{ref} = I_{Gr} R, \tag{2}$$

Temperature dependence of R is defined as:

$$R = R_O \cdot e^{-b(T-TO)}, \tag{3}$$

wherein $R_O$ is the resistance of the solid electrolyte body between the electrodes 4,5 at temperature $T_o$. As can be seen, the resistance decreases with increasing temperature, which means that the conductivity of the solid electrolyte body 1 increases with increasing temperature. This characteristic of the solid electrolyte 1 is well known. The factor b is a constant which is close to that of the constant a in formula 1.

Combining the equations (1) to (3) results in:

$$U_{ref} = I_{Gr,O} \cdot e^{a(T-To)} \cdot R_O e^{-b(T-TO)}. \tag{4}$$

The above equation (4) shows that the voltage drop across electrodes 4,5, which with electrolyte 1, form an ohmic resistance path becomes independent of temperature if exponents a and b are identical. Use of the second pair of electrodes 4,5, with the portion of the solid electrolyte body 1 therebetween thus permits measurement of the gas under conditions of compensation for temperature drift.

The exponents a and b in the equations (1), and (3), and (4) are not necessarily identical. By suitable choice, of the resistance $R_O$, for example by suitably arranging the relative sizes of the electrodes, the differences can be essentially compensated so that within the appropriate temperature range, essentially, complete compensation within the temperature range of operation of the sensor is obtained. Thus, by suitable selection of $R_O$, which can be readily determined by a simple resistance measurement, and using electrodes of appropriate size, the equation (4) can be brought into balance over the range of operating temperatures encountered in actual practise.

Various changes and modifications may be made within the scope of the inventive concept.

We claim:

1. Temperature and aging compensated polarographic sensing system to determine the oxygen content of gases, especially exhaust gases from an internal combustion engine comprising a single solid electrolyte body (1);
   a first electrode forming an anode electrode (3), applied to a first surface portion of said body, and exposed to the gases;

a second electrode forming a cathode electrode (2) applied to a second surface portion of the body spaced from said first surface portion by a first electrolyte body portion (1a);

voltage source means (7) furnishing a voltage, having one terminal (−) connected to one (2) of the electrodes, and second terminal (+) connected to the other one (3) of the electrodes (2, 3);

means (6) forming a diffusion barrier controlling access of oxygen molecules to the cathode electrode (2);

current sensing means (8) measuring the current in an oxygen ion sensing system formed by the voltage source means (7), the anode electrode (3), the solid electrolyte body between the first and the second surface portions of the solid electrolyte body and the cathode electrode (2) and providing an output indication of limit current flow as a function of diffusion of oxygen molecules through said diffusion barrier, and means for rendering the current independent of aging effects and temperature, comprising a third electrode (4) positioned on a third surface portion of said solid electrolyte body (1) spaced from said one of said electrodes by a second body portion (1b) and being serially connected between the other terminal (+) of the voltage source and said other one (3) of the electrodes (2, 3), said further electrode (4) and said second body portion (1b) of said solid electrolyte body (1) forming an oxygen ion conductive ohmic resistance which is serially connected between the cathode and anode electrodes (2, 3).

2. Oxygen content sensing system according to claim 1 wherein the voltage source means (7) is a controlled voltage source;

and means (10, 11) are provided for sensing (a) the voltage drop across the cathode and anode electrodes (2, 3), including the first body portion (1a), (b) the voltage drop across the further electrode (4) and the second body portion (1b);

and for comparing said voltage drops and for deriving a control signal, said control signal being applied to the controlled voltage source (7) to maintain the voltage across the electrodes (2, 3) at a value which renders current flow through the serial circuit formed by the oxygen ion sensing system (2, 1a, 3) and the ohmic resistance system (5, 1b, 4) independent of aging conditions of the electrodes (2, 3, 4, 5) applied thereto and of temperature variations of the resistance of the solid electrolyte body (1).

3. Oxygen content sensing system according to claim 2 wherein the voltage source means (7) applies a voltage across the electrodes (2, 3) at a constant value.

4. Oxygen content sensing system according to claim 3 wherein the voltage source means applies a voltage which has a value of between 0.5 to 1 V.

5. Oxygen content sensing system according to claim 2, wherein the solid electrolyte body is in the form of an elongated plate, the cathode and anode electrodes being applied to opposite surface portions of the plate in essentially transverse alignment, and a fourth electrode (5) is provided, positioned on a fourth surface portion oppositely and essentially transversely aligned with the third surface portion of the plate;

and means (9) connecting together the electrodes which are not connected to the voltage source (7).

6. Oxygen content sensing system according to claim 5, wherein said plate of solid electrolyte material comprises stabilized zirconium dioxide;

and the electrodes (2, 3, 4, 5) comprise a material selected from the group consisting of: platinum and a mixture of platinum and stabilized zirconium dioxide.

7. Oxygen content sensing system according to claim 5, wherein said sensing, comparing and control signal deriving means comprises a differential amplifier having one input connected to measure the voltage drop across the cathode and anode electrodes (2, 3) and the first body portion (1a), and another input connected to measure the voltage drop across the third electrode (4), and the second body portion (1b) and the fourth electrode (5), and providing an output control signal connected to and controlling said controlled voltage source.

8. Oxygen content sensing system according to claim 7, wherein said plate of solid electrolyte material comprises stabilized zirconium dioxide;

and the electrodes (2, 3, 4, 5) comprises a material selected from the group consisting of: platinum and a mixture of platinum and stabilized zirconium dioxide.

9. Oxygen content sensing system according to claim 2, wherein said sensing, comparing and control signal deriving means comprises a differential amplifier having one input connected to measure the voltage drop across the cathode and anode electrodes (2, 3) and the first body portion (1a), and another input connected to measure the voltage drop across the third electrode (4) and the second body portion (1b), and providing an output control signal connected to and controlling said controlled voltage source (7).

10. Oxygen content sensing system according to claim 1 wherein the solid electrolyte body is in the form of an elongated plate, the cathode and anode electrodes (2, 3) being applied to opposite surface portions of the plate in essentially transverse alignment, and a fourth electrode (5) is provided, positioned on a fourth surface portion oppositely and essentially transversely aligned with the third surface portion of the plate;

and means (9) connecting together the electrodes which are not connected to the voltage source (7).

11. Oxygen content sensing system according to claim 10 wherein said plate of solid electrolyte material comprises stabilized zirconium dioxide;

and the electrodes (2,3,4,5) comprise a material selected from the group consisting of: platinum and a mixture of platinum and stabilized zirconium dioxide.

12. Oxygen content sensing system according to claim 10, wherein said sensing, comparing and control signal deriving means comprises a differential amplifier having one input connected to measure the voltage drop across the cathode and anode electrodes (2, 3) and the first body portion (1a), and another input connected to measure the voltage drop across the third electrode (4), the second body portion (1b) and the fourth electrode (5), and providing an output control signal connected to and controlling said controlled voltage source.

13. Oxygen content sensing system according to claim 1, wherein a fourth electrode (5) is provided, located at a fourth surface portion of the body (1) and spaced from said first, second and third body portions;

and means (9) connecting together the fourth electrode and that one of the first, second, and third electrodes which is not connected to the voltage source.

14. Oxygen content sensing system according to claim 19, wherein said sensing, comparing and control signal deriving means comprises a differential amplifier having one input connected to measure the voltage drop across the cathode and anode electrodes (2, 3) and the first body portion (1a), and another input connected to measure the voltage drop across the third electrode (4) and the second body portion (1b), and providing an output control signal connected to and controlling said controlled voltage source (7).

15. Oxygen content sensing system according to claim 1, wherein said sensing, comparing and control signal deriving means comprises a differntial amplifier having one input connected to measure the voltage drop across the cathode and anode electrodes (2, 3) and the first body portion (1a), and another input connected to measure the voltage drop across the third electrode (4) and the second body portion (1b), and providing an output control signal connected to and controlling said controlled voltage source (7).

* * * * *